(12) United States Patent
Yamaoka (10) Patent No.: US 7,063,775 B2
(45) Date of Patent: Jun. 20, 2006

(54) BIOSENSOR AND METHOD FOR MANUFACTURING THE SAME

(75) Inventor: Hideaki Yamaoka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 428 days.

(21) Appl. No.: 10/276,473

(22) PCT Filed: May 15, 2001

(86) PCT No.: PCT/JP01/04055

§ 371 (c)(1),
(2), (4) Date: Nov. 14, 2002

(87) PCT Pub. No.: WO01/88526

PCT Pub. Date: Nov. 22, 2001

(65) Prior Publication Data

US 2003/0111344 A1    Jun. 19, 2003

(30) Foreign Application Priority Data

May 16, 2000 (JP) .............................. 2000-143340

(51) Int. Cl.
*G01N 27/327* (2006.01)
(52) U.S. Cl. .............................. 204/403.06; 204/403.05
(58) Field of Classification Search .......... 204/403.01, 204/403.02, 403.06, 403.14, 409, 415
See application file for complete search history.

(56) References Cited

U.S. PATENT DOCUMENTS

| | | | | |
|---|---|---|---|---|
| 4,388,166 A | * | 6/1983 | Suzuki et al. | 204/403.05 |
| 4,629,563 A | * | 12/1986 | Wrasidlo | 210/500.34 |
| 4,774,039 A | * | 9/1988 | Wrasidlo | 264/41 |
| 5,120,420 A | * | 6/1992 | Nankai et al. | 204/403.11 |
| 5,846,422 A | * | 12/1998 | Ditter et al. | 210/500.41 |
| 5,906,742 A | * | 5/1999 | Wang et al. | 210/500.41 |
| 5,916,156 A | * | 6/1999 | Hildenbrand et al. | 205/778 |
| 6,004,441 A | * | 12/1999 | Fujiwara et al. | 204/403.14 |
| 6,077,408 A | * | 6/2000 | Miyamoto et al. | 204/403.1 |
| 6,284,125 B1 | * | 9/2001 | Hodges et al. | 205/775 |
| 6,461,496 B1 | * | 10/2002 | Feldman et al. | 205/777.5 |
| 6,669,905 B1 | * | 12/2003 | Mathias et al. | 422/44 |
| 6,849,184 B1 | * | 2/2005 | Lampi et al. | 210/649 |
| 6,869,568 B1 | * | 3/2005 | Fogelman et al. | 422/56 |

FOREIGN PATENT DOCUMENTS

| | | |
|---|---|---|
| EP | 0849589 | 6/1998 |
| JP | 60-173458 | 9/1985 |
| JP | 09-101280 | 4/1997 |
| JP | 10-221293 | 8/1998 |
| JP | 11-344461 | 12/1999 |

OTHER PUBLICATIONS

Wikipedia entry for "polyethylene terephthalete." Downloaded on Nov. 16, 2005.*

* cited by examiner

*Primary Examiner*—Alex Noguerola
(74) *Attorney, Agent, or Firm*—Hamre, Schumann, Mueller & Larson, P.C.

(57) ABSTRACT

A biosensor (I) which comprises a capillary (3) having a passage (30) fined with an inlet (30a) for taking a sample solution therein, a membrane (8) for accelerating the transference of a sample solution in the passage (30), and a reaction portion (7) containing a reagent which reacts with a component to be detected in a sample solution.

16 Claims, 11 Drawing Sheets

BIOSENSOR AND METHOD FOR MANUFACTURING THE SAME

TECHNICAL FIELD

The present invention relates to a biosensor that is used when quantifying the concentration of a specific component contained in a liquid sample, for example a biological sample liquid such as blood or urine, and a manufacturing method thereof.

BACKGROUND ART

Figure 10:
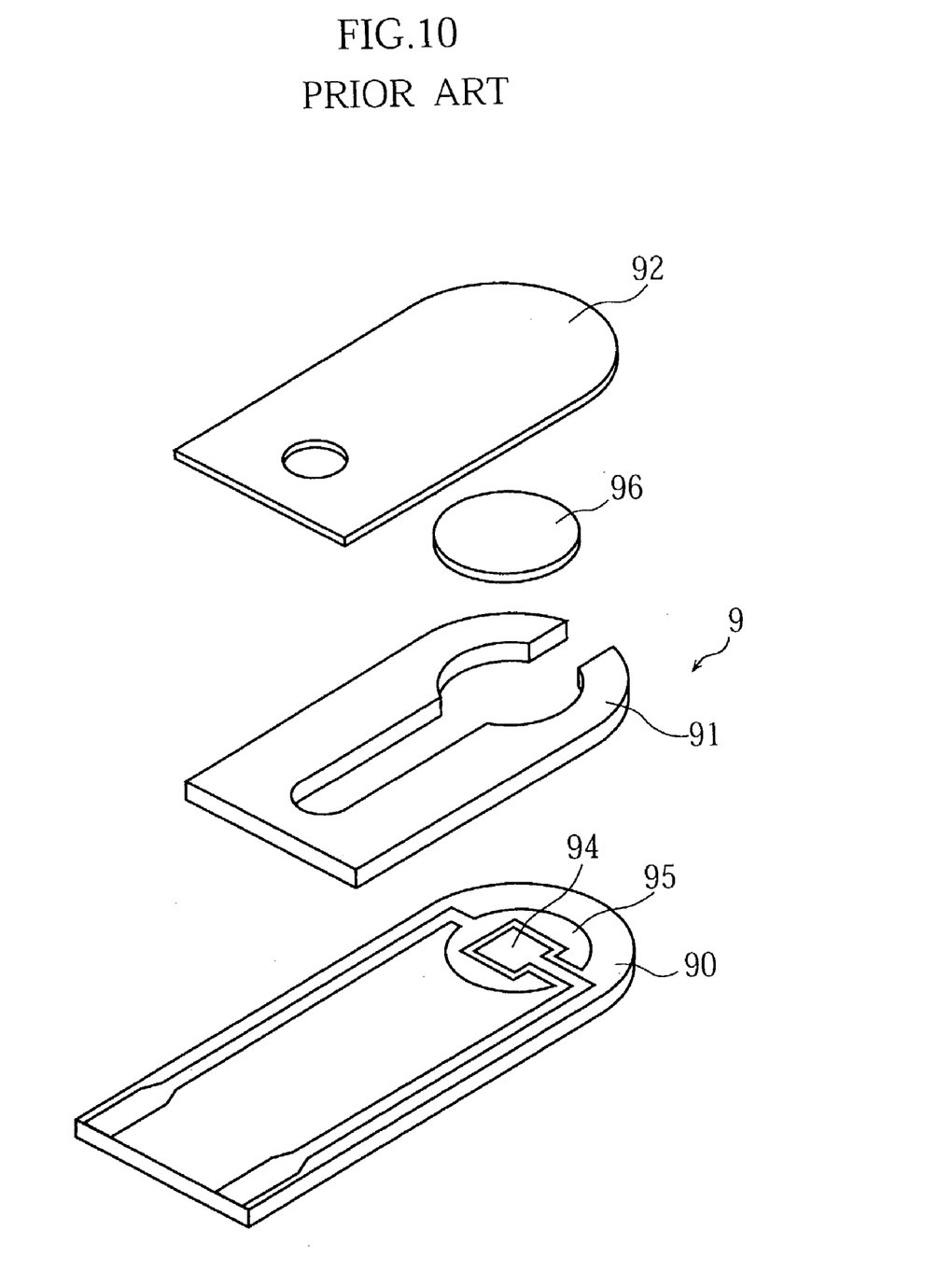
FIG. 10 is an exploded perspective view showing an example of a conventional biosensor.
Figure 11:
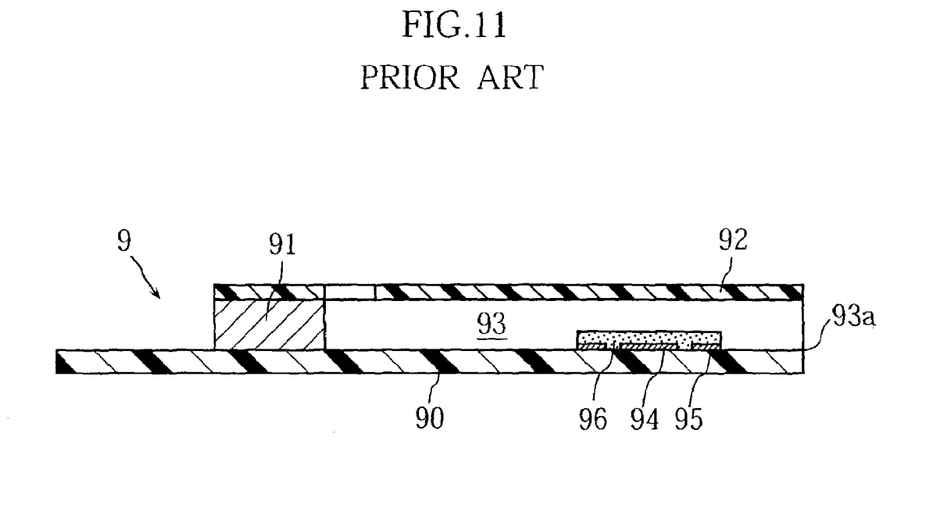
FIG. 11 is a sectional view of the biosensor of FIG. 10 in an assembled state.

As a disposable biosensor, a capillary type biosensor that is constituted such that a sample liquid is fed to a reaction part using a capillary phenomenon is known. FIG. 10 is an exploded perspective view of such a conventional biosensor 9, and FIG. 11 is a sectional view of the assembled biosensor 9. The biosensor 9 has a structure in which an insulating base 90, a spacer 91 and a cover 92 are built up on top of one another. As shown in FIG. 11, a capillary 93 having an inlet port 93a is defined by the spacer 91 between the base 90 and the cover 92. A working electrode 94, a counter electrode 95, and a reaction part 96, which is formed on top of the working electrode 94 and the counter electrode 95, are provided inside the capillary 93. The reaction part 96 contains any of various reagents necessary for a prescribed reaction system, for example a redox enzyme, in accordance with the subject of quantification.

With a biosensor 9 having such a structure, the sample liquid moves from the inlet port 93a through the capillary 93 due to a capillary phenomenon, and reaches the reaction part 96. The reagent contained in the reaction part 96 then dissolves in the sample liquid, and a redox reaction occurs. By measuring the oxidation current at this time, the concentration of a specific component in the sample liquid is quantified.

However, with the conventional biosensor 9, there has been a problem that if a solid component in the sample liquid is present in the vicinity of the working electrode 94 or the counter electrode 95, then the measured current value is affected, bringing about a worsening of the measurement precision.

Figure 12:
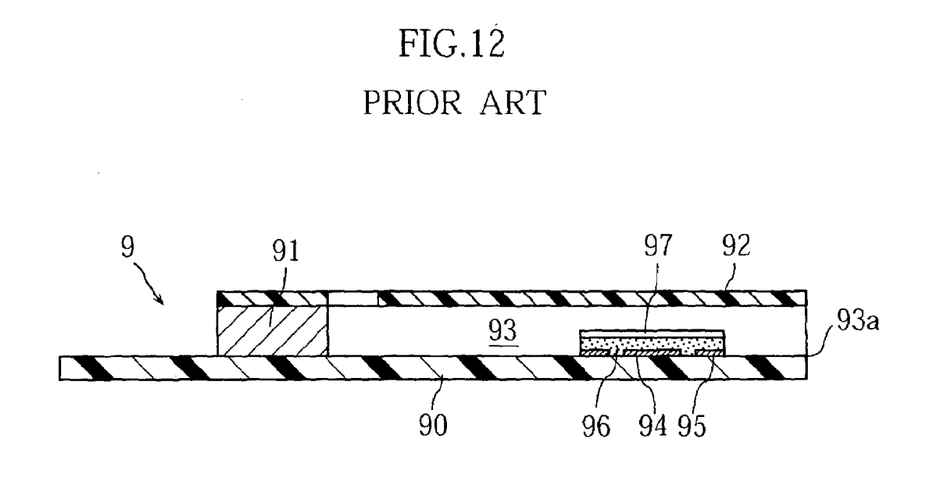
FIG. 12 is a sectional view showing another example of a conventional biosensor.

Art of which an object is to avoid the effects on the measured current due to such a solid component is disclosed in Japanese Patent Application Laid-open No. 11-344461 Official Gazette. As shown in FIG. 12 of the present application, the biosensor disclosed in this official gazette has a structure in which a filter 97 constituted from a fibrous material such as fiberglass is further formed on top of the reaction part 96 of the biosensor of FIG. 11. The filter 97 is formed for example by making the fibrous material into a single body such as a fleece or a felt. The sample liquid that has moved through the capillary 93 thus dissolves the reaction part 96 after the solid component has been filtered out by the filter 97, and then reaches the working electrode 94 and the counter electrode 95. One would presume that it would be difficult to make the sample liquid flow adequately and filter out the solid component at the fibrous filter 97 in the case that the viscosity of the sample liquid is high, and hence according to Japanese Patent Application Laid-open No. 11-344461 Official Gazette, a surfactant is contained in the filter 97 to make the movement of the sample liquid through the filter 97 easy and make the filtering out of the solid component by the filter 97 progress smoothly.

However, if a surfactant is present in the filter 97, then in the case for example that whole blood is used as the sample liquid, hemolysis occurs when the blood passes through the filter 97, and hence the blood cell component that leaches out from the blood cells influences the measurement results. As a result, the accuracy of the measurements drops.

Moreover, the cover 92, which is one of the members defining the capillary 93, is generally formed from a resin material such as polyethylene terephthalate (PET). However, PET is a hydrophobic material, and hence there is a tendency for the movement of the sample liquid through the capillary 93 to be inhibited. When the sample liquid is taken into the capillary 93, a sufficient amount and a sufficient speed thus cannot be achieved, and hence a situation may arise in which the concentration of the specific component cannot be measured accurately.

DISCLOSURE OF THE INVENTION

It is an object of the present invention to eliminate or mitigate the problems described above. Specifically, it is an object of the present invention to provide a capillary type biosensor according to which the movement of a sample liquid through the capillary can be promoted and the concentration of a specific component in the sample liquid can be measured accurately, and a method for manufacturing such a biosensor.

A first aspect of the present invention provides a biosensor. This biosensor comprises a capillary having a channel with an inlet port for taking in a sample liquid, a membrane for promoting the movement of the sample liquid through the channel, and a reaction part containing a reagent that reacts with a component to be tested in the sample liquid whose movement has been promoted by the membrane.

There are no particular limitations on the place of formation of the membrane. The membrane can be provided anywhere, so long as it is inside the capillary. Moreover, the membrane may be provided over all of the internal walls of the capillary.

Preferably, the membrane is provided in the vicinity of the inlet port.

Preferably, the membrane has a plurality of pores each of which is no less than 0.25 μm but no more than 45 μm.

Preferably, the membrane is laminated on the reaction part.

Preferably, the reaction part and the membrane are formed to extend to the inlet port.

Preferably, the membrane is an asymmetric membrane or composite membrane comprising, thicknesswise, a first layer having smaller pores, and a second layer having larger pores. The first layer is held in contact with the reaction part. Particularly preferably, the membrane is an asymmetric membrane made of a polysulfone.

Preferably, the pores of the first layer have a pore diameter of no less than 0.25 μm but no more than 0.45 μm, and the pores of the second layer have a pore diameter of no less than 25 μm but no more than 45 μm.

Preferably, the capillary has an opening serving as an air escape hole.

Preferably, the capillary has a transparent part or semi-transparent part for internally observing the capillary.

Preferably, the membrane is white.

Preferably, the biosensor further comprises an elongate working electrode and an elongate counter electrode on an insulating base. The capillary is formed to intersect the working electrode and the counter electrode on the insulating base.

Preferably, the counter electrode is generally parallel to the working electrode.

Preferably, the capillary comprises a pair of upright walls on the base, and a cover bridging the pair of walls.

According to a second aspect of the present invention, a method is provided for manufacturing a biosensor which comprises a capillary having a channel with an inlet port for taking in a sample liquid, a membrane for promoting the movement of the sample liquid through the channel, and a reaction part containing a reagent that reacts with a component to be tested in the sample liquid whose movement has been promoted by the membrane. This method comprises a step of forming a working electrode and a counter electrode in an elongate shape on an insulating base, a step of forming an elongate reaction part intersecting the working electrode and the counter electrode, a step of forming an elongate membrane on the reaction part, a step of providing a pair of walls along longitudinal edges on both sides of the reaction part and the membrane, and a step of forming a capillary by forming a cover bridging the pair of walls.

Preferably, the pair of walls is formed by applying a hot melt adhesive.

Preferably, the pair of walls is formed by sticking double-sided tape onto the insulating base.

Other features and advantages of the present invention will become more apparent from the following detailed description while referring to the accompanying drawings.

BEST MODE FOR CARRYING OUT THE INVENTION

A biosensor 1 according to the present invention will now be described with reference to FIGS. 1 to 3. The biosensor 1 includes an insulating base 2 which is formed in a strip shape (e.g. 6×30×0.25 mm) from a glass epoxy resin or the like. A capillary 3 that extends widthwise of the insulating base 2 (the X-direction in FIG. 1) is formed on top of the insulating base 2.

The capillary 3 is essentially defined by an electrode system 4, a pair of spacers 5, and a cover 6, which are provided on top of the insulating base 2. Inside the capillary 3, a reaction part 7 is formed on the electrode system 4, and a membrane 8 is further formed on the reaction part 7.

Figure 1:
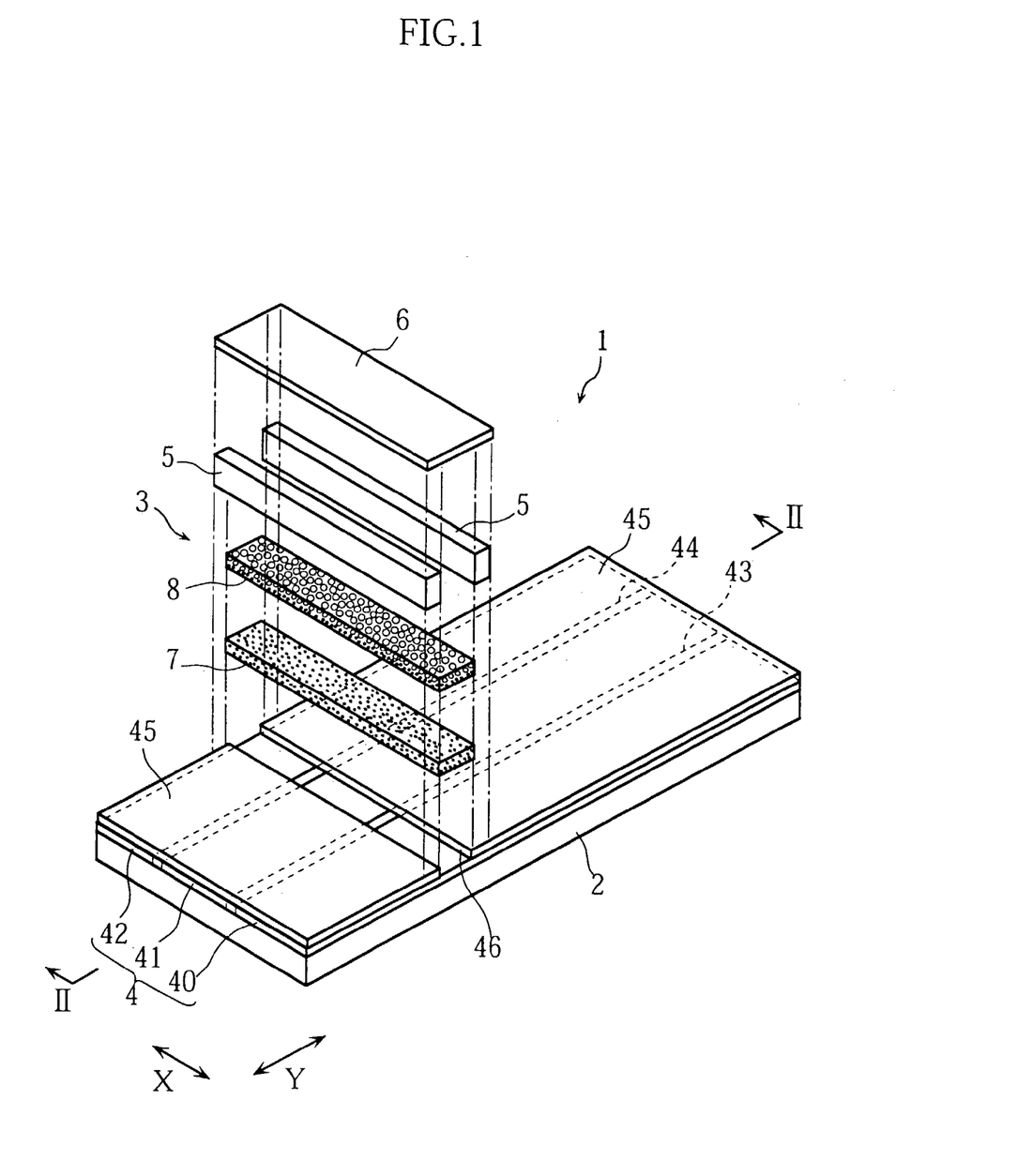
FIG. 1 is a partially exploded perspective view of a biosensor according to a first aspect of the present invention.

As is shown clearly in FIG. 1, the electrode system 4 comprises a counter electrode 40, a working electrode 41 and a reference electrode 42, each of which extends longitudinally of the insulating base 2 (the Y-direction in FIG. 1). An inter-electrode insulator 43 is provided between the counter electrode 40 and the working electrode 41. Similarly, an inter-electrode insulator 44 is provided between the working electrode 41 and the reference electrode 42. These inter-electrode insulators 43 and 44 are flush with the electrodes 40, 41 and 42. The electrodes 40, 41 and 42 are each formed to a thickness of approximately 40 µm and a width of approximately 2 mm using a technique such as screen printing, sputtering or vapor deposition. An insulating layer 45 of thickness approximately a few tens of µm is further formed on top of the electrodes 40, 41 and 42 and the inter-electrode insulators 43 and 44. The insulating layer 45 is divided by a groove part 46 that extends in the width direction of the insulating base 2. The groove part 46 has a width of approximately 0.5 to 1.5 mm.

The reaction part 7 is a solid material that contains an enzyme that reacts with a specific component (substrate) contained in a biological sample liquid such as blood, and is constituted such as to dissolve when impregnated with the sample liquid. As is shown clearly in FIGS. 2 and 3, the reaction part 7 is filled into the groove part 46, with the thickness of the reaction part 7 being made to be approximately a few tens of µm. In the case that a redox enzyme is used as the enzyme, an electron acceptor may be put into the reaction part 7 in advance.

Figure 3:
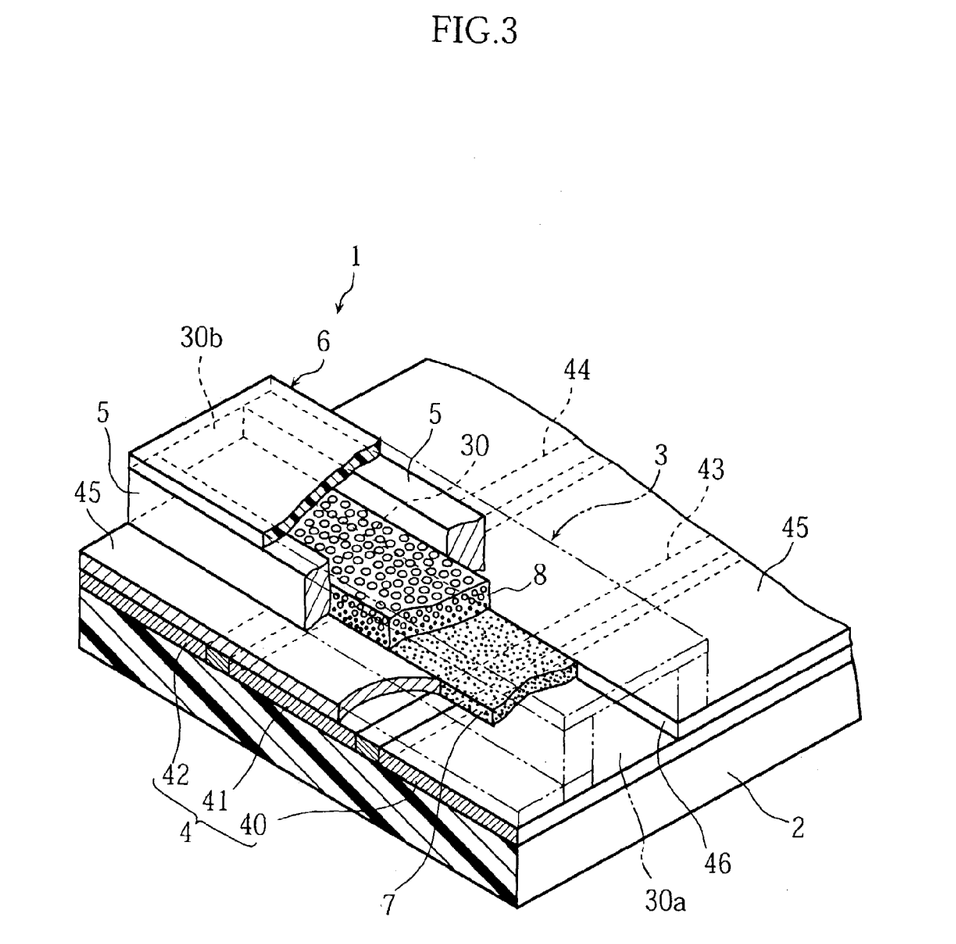
FIG. 3 is a partially broken open perspective view in which principal portions of the biosensor of FIG. 1 in an assembled state are enlarged.

As is shown clearly in FIG. 3, the membrane 8 is disposed on top of the reaction part 7 such as to extend in the width direction of the insulating base 2, is white, and has a thickness of approximately 130 µm. The membrane 8 is a porous synthetic polymer membrane, and can form a porous membrane having a smaller pore diameter than a glass filter. In the present embodiment, the diameter of the plurality of pores in the membrane 8 is at least 0.25 µm but not more than 45 µm. As the membrane 8, for example one containing a polysulfone type raw material, an aromatic polyamide type raw material, cellulose acetate or the like can be adopted.

Moreover, an asymmetric membrane or composite membrane can be used as the membrane 8. Here, an asymmetric membrane is a membrane in which a support layer in which large-diameter pores are formed and a dense layer in which small-diameter pores are formed are provided in the same material. On the other hand, a composite membrane is a membrane in which a support layer in which large-diameter pores are formed and a dense layer in which small-diameter pores are formed are provided basically as separate materials.

In the case of using an asymmetric membrane or composite membrane as the membrane 8, the membrane 8 is disposed such that the dense layer is in contact with the reaction part 7. Preferably, the diameter of the plurality of pores formed in the dense layer is at least 0.25 µm but not more than 0.45 µm. Preferably, the diameter of the plurality of pores formed in the porous layer is at least 25 µm but not more than 45 µm.

As is shown clearly in FIG. 3, each of the pair of spacers 5 are disposed extending in the width direction of the insulating base 2 along the two side edges of the reaction part 7 and the membrane 8 so as to sandwich the membrane 8 therebetween. The spacers 5 are thicker than the membrane 8, having for example a thickness of approximately 200 µm.

The cover 6 bridges between the pair of spacers 5. The cover 6 is a transparent member or a semitransparent member formed from a resin such as polyethylene terephthalate (PET), and has a thickness of approximately 15 to 30 µm.

Figure 2:
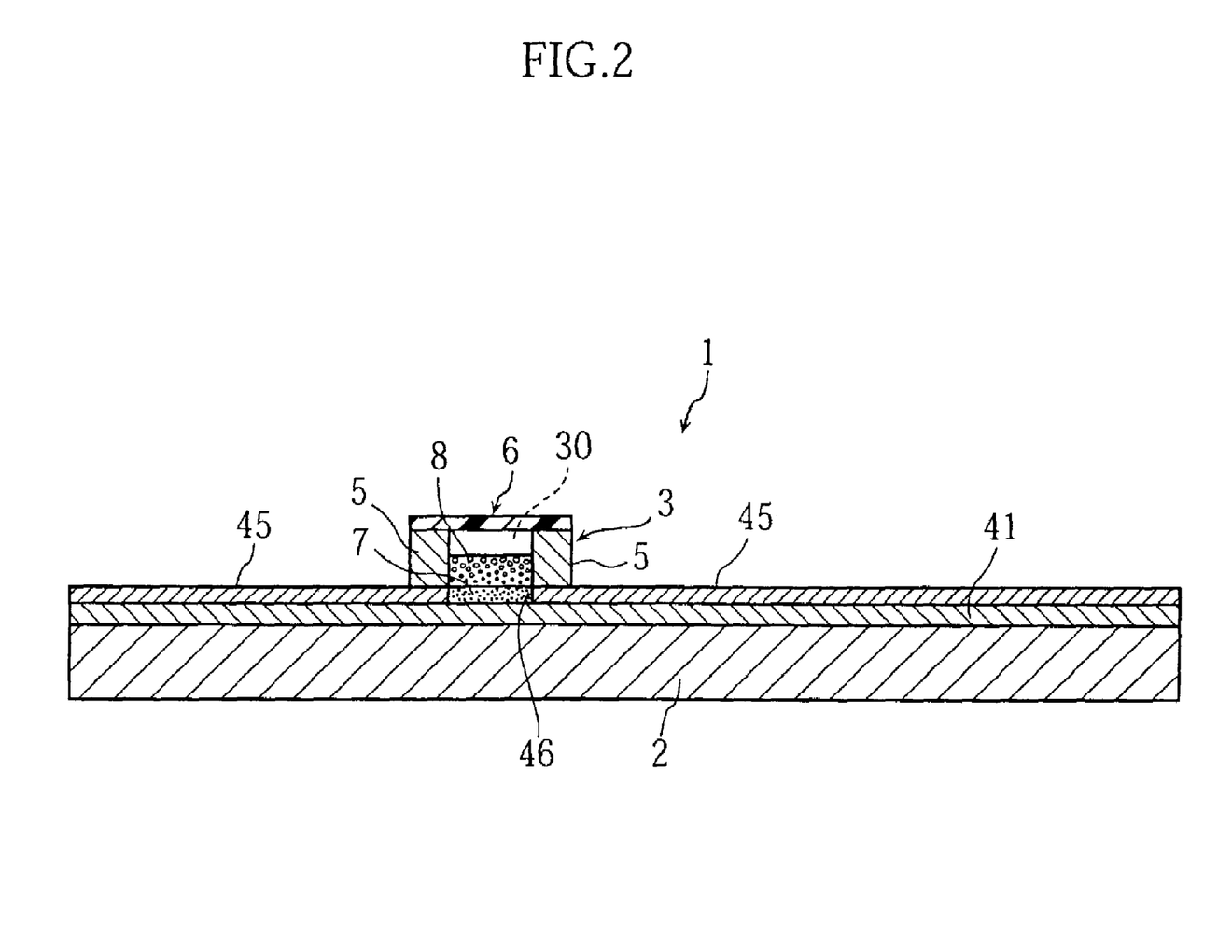
FIG. 2 is a sectional view along line II–II of the biosensor of FIG. 1 in an assembled state.

As is shown clearly in FIG. 2, a channel 30 is formed between the cover 6 and the membrane 8, with the height of the channel 30 being approximately 50 µm. As is shown clearly in FIG. 3, the two ends of the channel 30 are open at openings 30a and 30b of the capillary 3. One opening 30a functions as an inlet port for introducing the sample liquid into the capillary 3. The other opening 30b functions as an escape route for air in the capillary 3 when the sample liquid moves through the capillary 3, and as a result a good capillary phenomenon is secured in the channel 30.

With the biosensor 1 constituted in this way, if the sample liquid such as blood is introduced from the opening 30a of the capillary 3, then the sample liquid moves through the channel 30 toward the opening 30b side due to a capillary phenomenon that acts in the longitudinal direction of the capillary 3. The amount of the sample liquid required in this case is for example 0.2 to 1.5 µl. A part of the sample liquid introduced into the capillary 3 comes into contact with the membrane 8. A suction force acts on the sample liquid in contact with the surface of the membrane 8, and hence the sample liquid moves through the pores of the membrane 8 toward the reaction part 7. As the sample liquid moves from pore to pore through the membrane 8, a suction force acts to also pull the following sample liquid in the channel 30 into the membrane 8. As a result, the movement of the sample liquid through the channel 30 is promoted, and hence it becomes easy to make the sample liquid reach every region of the reaction part 7.

It is thought that the suction force that acts on the sample liquid is due to a capillary phenomenon that arises in the pores; the size of the suction force is thus proportional to the surface tension of the sample liquid, and is inversely proportional to the diameter of the pores. Consequently, adopting a measure that reduces the surface tension of the sample liquid such as making the membrane 8 contain a surfactant will inhibit the movement of the sample liquid through the capillary 3. With the biosensor 1, it is thus best not to carry out hydrophilic treatment on the membrane 8 such as making the membrane 8 contain a surfactant even in the case that the sample liquid has a high viscosity. If hydrophilic treatment is not carried out on the membrane 8, then there is an advantage from the standpoint of the manufacturing cost commensurate with this. In addition, in the case that a surfactant is not included in the membrane 8, even in the case that the sample liquid is whole blood, there is no need to worry about a drop in the measurement accuracy due to hemolysis.

In the case that an asymmetric membrane or composite membrane is used as the membrane 8, and the membrane 8 is installed such that the side with the large pores is exposed at the channel 30 and the side with the small pores is in contact with the reaction part 7, the movement of the sample liquid through the channel 30 can be further promoted. Specifically, if the pore diameter in the vicinity of the channel 30 is larger, then there is a tendency for the introduction/penetration of the sample liquid into the membrane 8 to be improved, and if the pore diameter in the vicinity of the reaction part 7 is smaller, then there is a tendency for a good capillary phenomenon to arise throughout the whole membrane 8, and thus the force sucking the sample liquid can be kept large. As a result, a larger amount of the sample liquid can be fed faster to the reaction part 7 via the channel 30 and the membrane 8.

With the present embodiment, the reaction part 7 and the membrane 8 on top thereof are formed up to the opening 30a, and hence the sample liquid introduced from the opening 30a comes into contact with the membrane 8 and some of the sample liquid moves into the pores of the membrane 8 immediately. The movement of the sample liquid through the channel 30 is then promoted by the movement of the sample liquid into the membrane 8. Consequently, even with a small amount of sample liquid, the sample liquid arrives at the reaction part 7 instantly and reliably.

With the present embodiment, the cover 6 is made to be transparent, and the membrane 8 is made to be white. According to this constitution, it can easily be checked from the outside via the cover 6 how far the sample liquid has filled into the channel 30. Such visual checking is possible even if the electrodes 40, 41 and 42 are formed from carbon black or the like so as to be black, and even if the sample liquid is red as in the case of blood. Moreover, the position that the sample liquid has reached can also be identified by detecting the state of electrical continuity between the electrodes 40, 41 and 42. This is because as the sample liquid moves through the capillary 3 from the opening 30a to the opening 30b while impregnating into the membrane 8 and the reaction part 7, the state of electrical continuity between the electrodes 40, 41 and 42 via the sample liquid changes.

The sample liquid that has passed through the membrane 8 is impregnated into the reaction part 7. At this time, the reaction part 7 dissolves in the sample liquid, and the enzyme contained in the reaction part 7 and the specific component (substrate) in the sample liquid react with one another. In the case that a redox enzyme is used as the enzyme and an oxidation reaction of the substrate is used, the constitution can be made to be such that dissolved oxygen in the sample liquid is reduced to hydrogen peroxide at the same time as the substrate is oxidized. In the case of such a constitution, if a prescribed voltage is applied between the counter electrode 40 and the working electrode 41 after a certain time has elapsed, then the hydrogen peroxide is oxidized and hence a response current is generated. The amount of hydrogen peroxide produced is proportional to the concentration of the specific component in a certain volume of the sample liquid, and hence by measuring the response current the concentration of the specific component in the sample liquid can be determined. Moreover, in the case that the reaction part 7 has been made to contain an electron acceptor in an oxidized state, the electron acceptor is reduced instead of the above-mentioned dissolved oxygen at the same time as the specific component is oxidized by the enzyme. In this case, if a prescribed voltage is applied between the counter electrode 40 and the working electrode 41, then the reduced form of the electron acceptor thus turns back into the oxidized form, and the concentration of the specific component in the sample liquid can be measured from the response current at this time. Moreover, the concentration of the specific component may also be calculated based on a predetermined calibration curve that shows the relationship between the response current and the concentration of the specific component.

The application of the voltage to the electrodes 40, 41 and 42 and the measurement of the response current are carried out in a state in which the biosensor 1 is loaded into a measuring apparatus provided separately to the biosensor 1, and measurement terminals of the measuring apparatus and the electrodes 40, 41 and 42 of the biosensor 1 are electrically connected together. With the biosensor 1 described above, each of the counter electrode 40, the working electrode 41 and the reference electrode 42 is covered by an insulating layer 45 even at the two end parts, and hence the application of the voltage and the measurement of the response current are carried out using parts that are exposed at an end face of the biosensor 1. However, to make the application of the voltage to the electrodes 40, 41 and 42 and the measurement of the current easier, it is also possible to remove parts of the insulating layer 45 to expose part of each of the electrodes 40, 41 and 42 in advance, or to adopt a constitution in which the insulating layer 45 is not formed at all.

Next, a method of manufacturing biosensors 1 as shown in FIGS. 1 to 3 will be described with reference to FIGS. 4 to 9.

Figure 4:
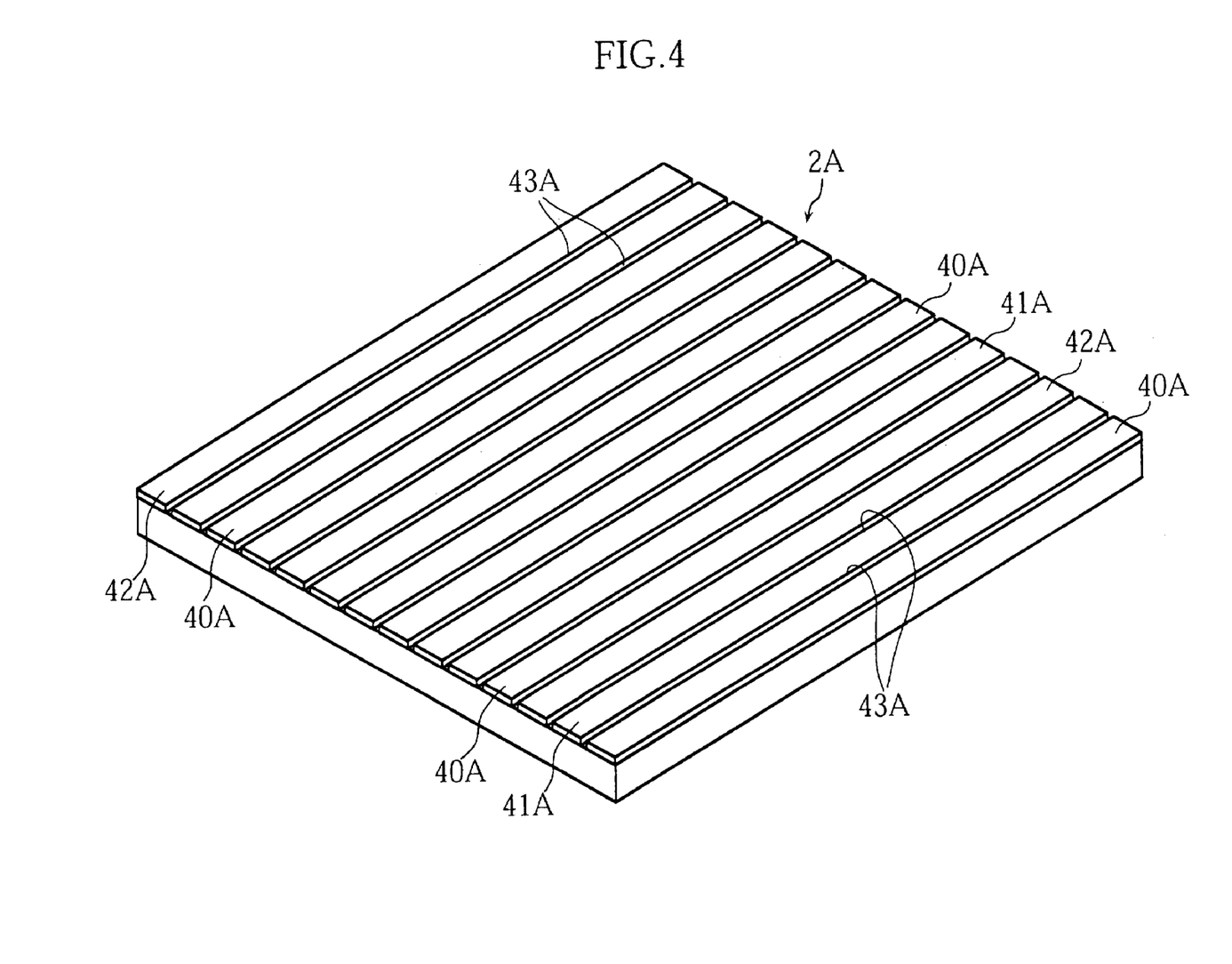
FIG. 4 is a perspective view for explaining a step included in a method of manufacturing a biosensor according to a second aspect of the present invention.

First, as shown in FIG. 4, conductor layers 40A, 41A and 42A that will ultimately become counter electrodes 40, working electrodes 41 and reference electrodes 42 are formed in a state divided by grooves 43A on a mother base 2A made of a glass epoxy resin, a ceramic or the like. The conductor layers 40A, 41A and 42A can be formed individually by a technique such as screen printing, sputtering or vapor deposition. Alternatively, the conductor layers 40A, 41A and 42A can be formed simultaneously by forming a conductor layer over the whole surface of the mother base 2A and then providing a plurality of grooves 43A in the conductor layer. The conductor layers 40A, 41A and 42A are each formed from carbon black, copper, silver, gold or the like, and have a thickness of for example approximately 40 μm.

Figure 5:
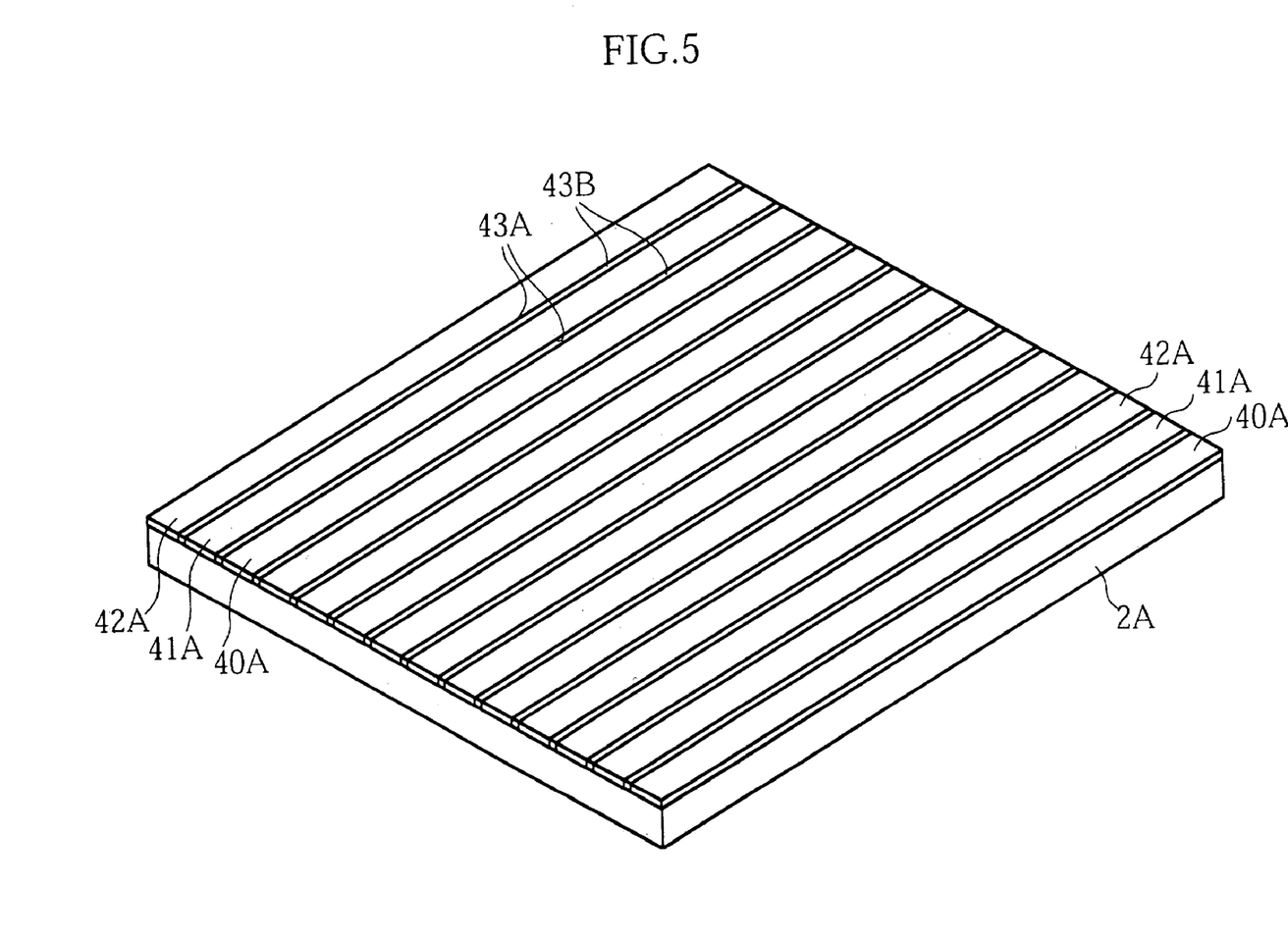
FIG. 5 is a perspective view for explaining a step following on from FIG. 4.
Figure 6:
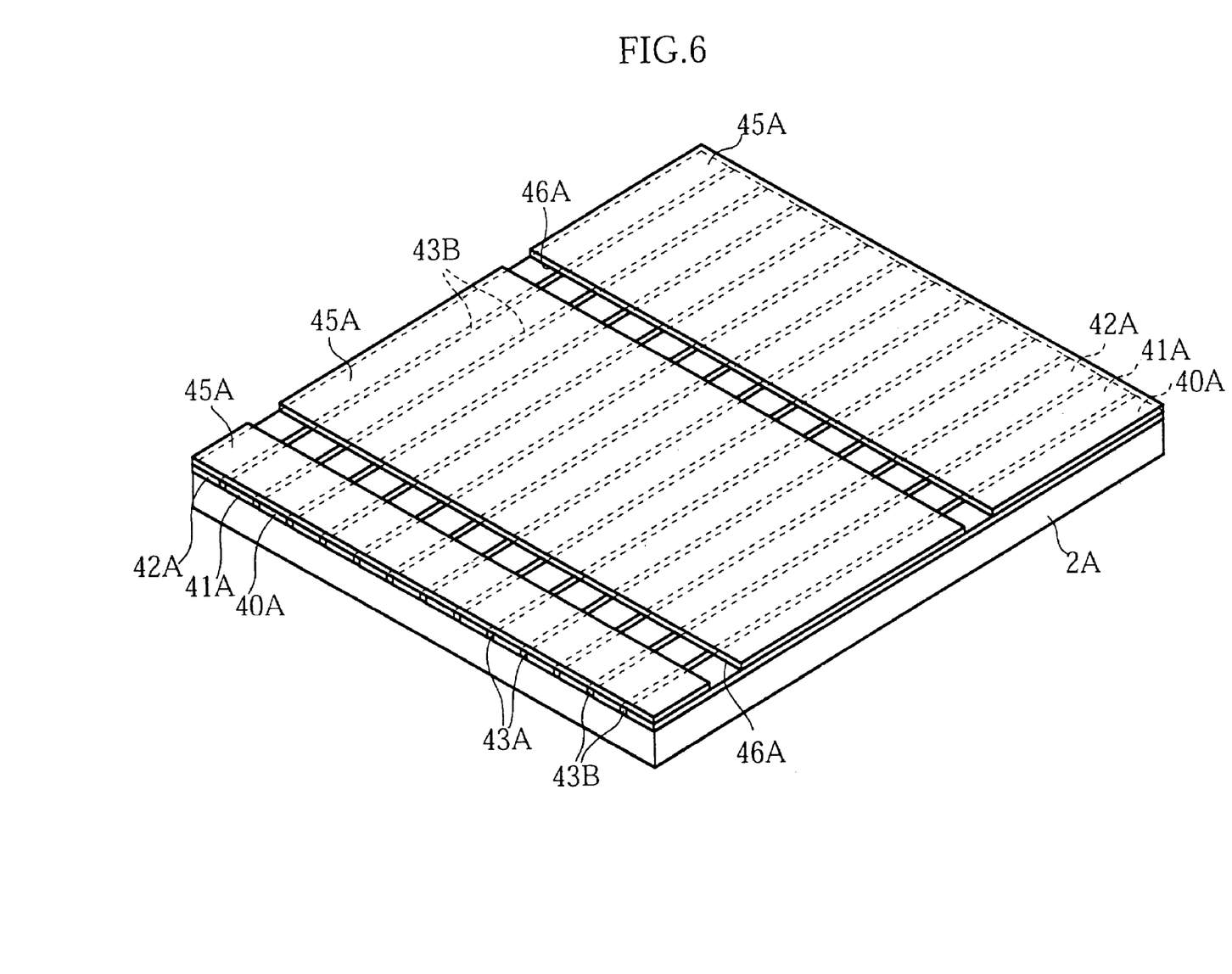
FIG. 6 is a perspective view for explaining a step following on from FIG. 5.

Next, as shown in FIG. 5, insulators 43B are formed by filling an insulating material into the grooves 43A. Then, as shown in FIG. 6, insulating layers 45A are formed in a state divided by groove parts 46A that are orthogonal to the conductor layers 40A, 41A and 42A. The insulators 43B and the insulating layers 45A may be formed separately, but can also be formed simultaneously. In the case of forming the insulators 43B and the insulating layers 45A simultaneously, for example an insulating material is applied onto the surfaces of the conductor layers 40A, 41A and 42A and at the same time the insulating material is filled into the grooves 43A, and then the groove parts 46A are formed by carrying out etching or the like. Alternatively, it is also possible to form a mask in regions corresponding to the groove parts 46A, and then form the insulators 43B and the insulating layers 45A simultaneously by screen printing.

Figure 7:
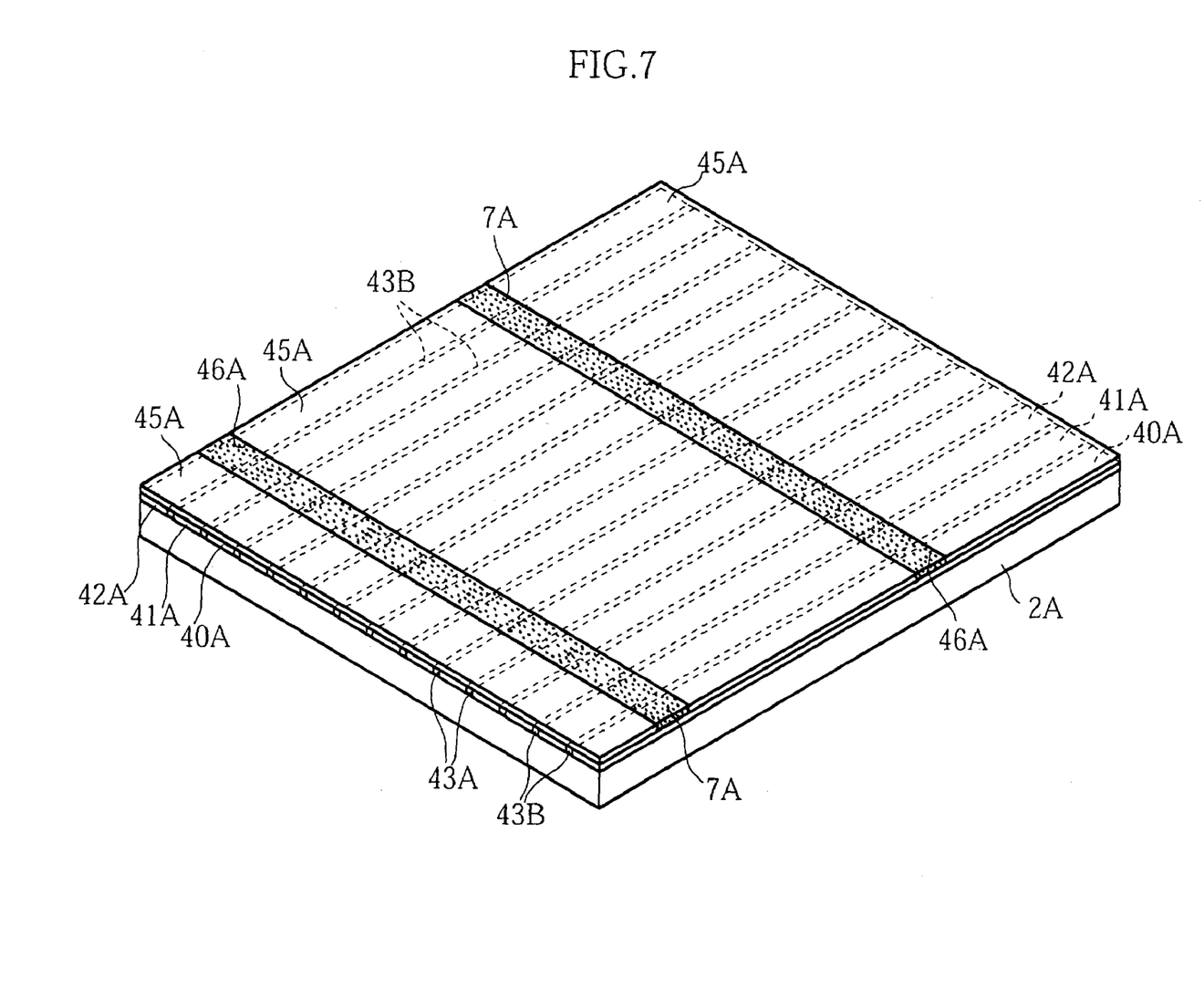
FIG. 7 is a perspective view for explaining a step following on from FIG. 6.

Next, as shown in FIG. 7, reaction layers 7A that will become reaction parts 7 are formed so as to fill up the groove parts 46A. These reaction layers 7A are formed, for example, by filling the groove parts 46A with an aqueous solution of an enzyme that has been selected in accordance with the specific component to be quantified, or a mixed aqueous solution of such an aqueous solution and a hydrophilic polymer, and then drying. The reaction layers 7A have a thickness of for example approximately a few tens of μm.

Here, examples of the enzyme used include glucose oxidase, fructose oxidase, lactic acid oxidase, and cholesterol oxidase. In the case of using a redox enzyme, the reaction parts 7 may be made to contain an electron acceptor; examples of such an electron acceptor include ferricyan ions, p-benzoquinone and derivatives thereof, phenazine methosulfate, methylene blue, and ferrocene and derivatives thereof.

Examples of the hydrophilic polymer constituting the mixed solution include carboxymethyl cellulose, hydroxyethyl cellulose, hydroxypropyl cellulose, methyl cellulose, ethyl cellulose, ethyl hydroxyethyl cellulose, carboxymethyl ethyl cellulose, polyvinyl pyrrolidone, polyvinyl alcohol, polyamino acids such as polylysine, polysulfonic acid, gelatin and derivatives thereof, polyacrylic acid and salts thereof, polymethacrylic acid and salts thereof, starches and derivatives thereof, and polymers of maleic anhydride and salts thereof.

Figure 8:
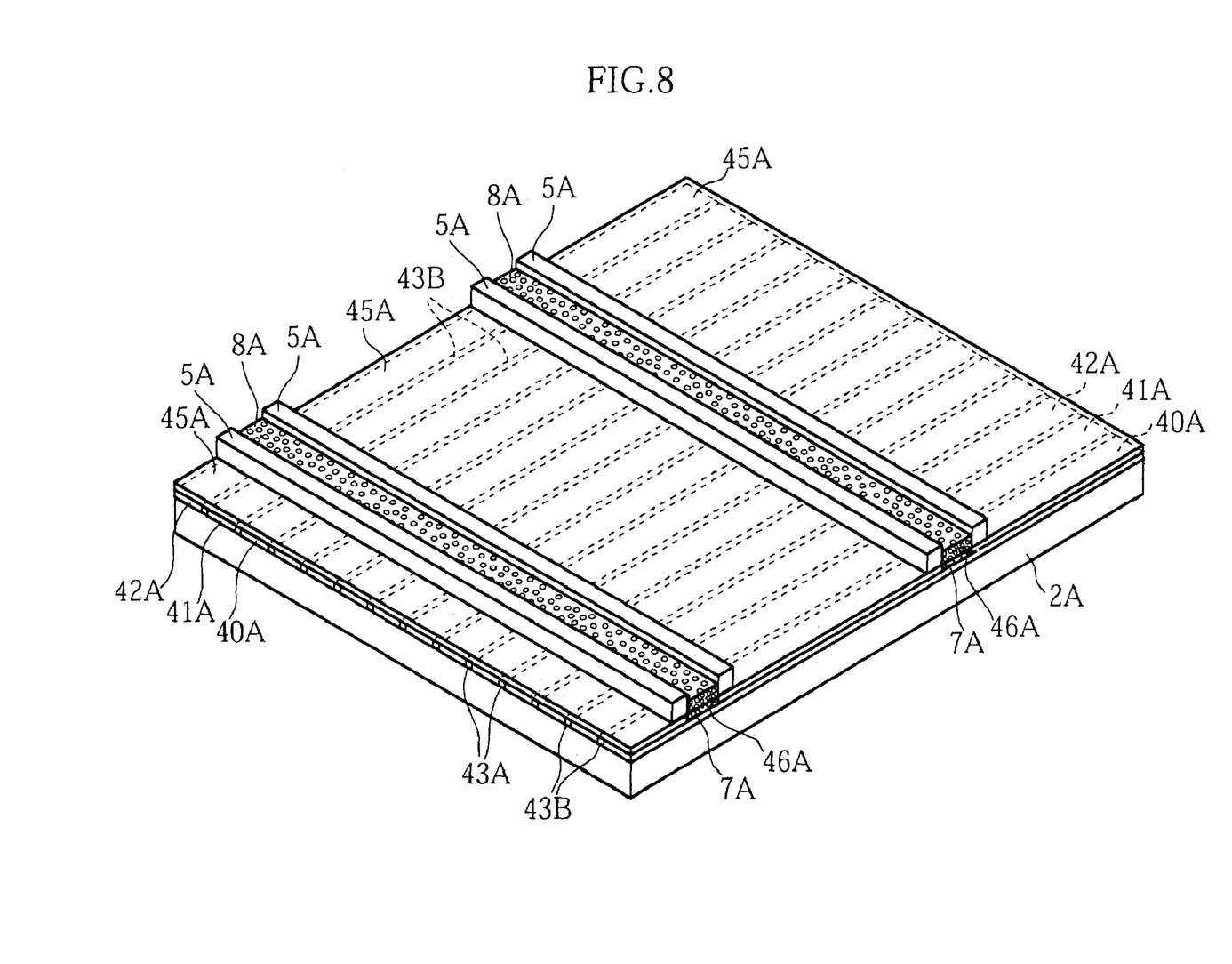
FIG. 8 is a perspective view for explaining a step following on from FIG. 7.

Next, as shown in FIG. 8, membrane layers 8A that will become membranes 8 are disposed on top of the reaction layers 7A, and adhesive layers 5A are formed on both sides of each of the membrane layers 8A.

The membrane layers 8A have a thickness of for example approximately 130 μm, with the width and length matching those of the reaction layers 7A.

The adhesive layers 5A are formed for example by applying a hot melt adhesive, or by sticking on double-sided tape. The adhesive layers 5A in the present embodiment are provided either side of each membrane layer 8A, but may also be provided such that parts thereof are formed on top of side edge parts of the reaction layers 7A or the membrane layers 8A. The thickness (height) of the adhesive layers 5A is for example approximately 200 μm.

Figure 9:
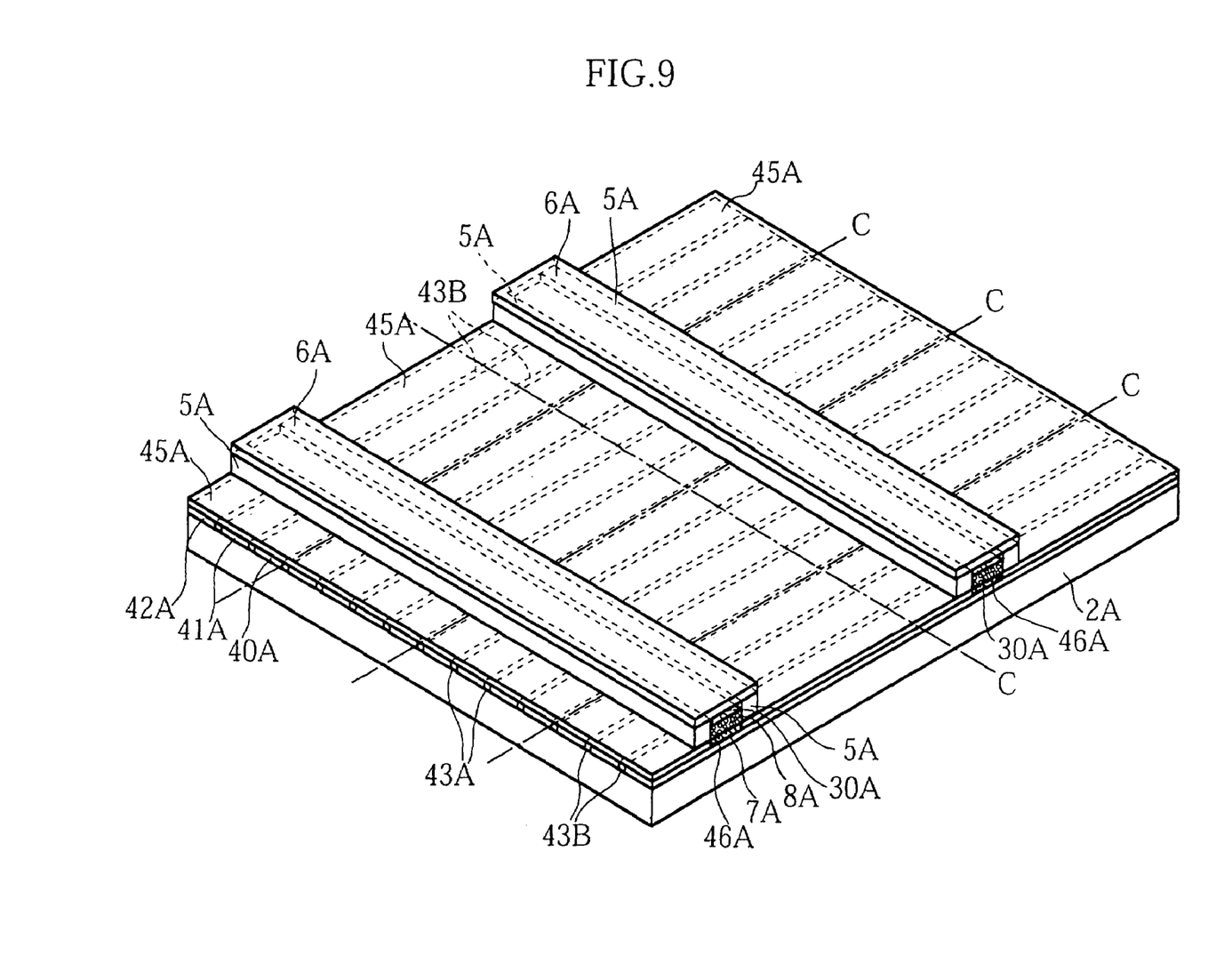
FIG. 9 is a perspective view for explaining a step following on from FIG. 8.

Next, as shown in FIG. 9, a cover 6A is fixed onto each pair of adhesive layers 5A that have a membrane layer 8A sandwiched therebetween, so as to bridge between the adhesive layers 5A. Spaces 30A that will become channels 30 are thus formed between the covers 6A and the membrane layers 8A.

The covers 6A are formed for example from PET so as to be transparent, and have a thickness of approximately 15 to 30 μm. In the case where a hot melt adhesive or double-sided tape has been used as the adhesive layers 5A, the covers 6A can be fixed onto the spacers 5A through the adhesiveness of the adhesive layers 5A.

Finally, the mother base 2A is cut along the alternate long and short dash lines C shown in FIG. 9, whereby a plurality of biosensors 1 as shown in FIGS. 1 to 3 are obtained simultaneously.

Note that the numbers and lengths of the conductor layers 40A, 41A and 42A, the reaction layers 7A, the membrane layers 8A and so on are changed as appropriate in accordance with the size and number of the biosensors 1 to be manufactured.

Table 1 shows the results of measuring the time required for a sample liquid to be filled more-or-less completely into the capillary for the biosensor 1 according to the present invention in which the membrane 8 is provided on top of the reaction part 7 and a biosensor having exactly the same structure except that the membrane is not provided. A membrane of product number SD450 made by Memtec was used as the membrane 8. The measurements were carried out using three sample liquids exhibiting different hematocrits to one another. The volume of the channel in the capillary of each of the biosensors was made to be 6 mm×0.5 mm×130 μm. The thickness of the membrane of the biosensor 1 was made to be 130 μm. The measurement values in Table 1 are the mean values over three samples.

TABLE 1

|  | Hematocrit 47 | Hematocrit 77 | Hematocrit 80 |
| --- | --- | --- | --- |
| With membrane | 1.20s | 1.80s | 4.20s |
| Without membrane | 1.30s | 2.60s | 7.20s |

As is clear from Table 1, in the case that the membrane 8 was used, the filling speed of the sample liquid into the capillary was higher than in the case that the membrane 8 was not used. In particular, the difference was more marked the higher the hematocrit (the higher the viscosity) of the sample. In this way, with the biosensor 1 in which the membrane 8 is provided on top of the reaction part 7, a sample liquid can be made to reach every region of the capillary 3 rapidly and reliably even in the case that the sample liquid has a high viscosity.

The invention claimed is:

1. A biosensor, comprising:
   a capillary having a channel with an inlet port for taking in a sample liquid;

a membrane for promoting movement of said sample liquid through said channel, the membrane being asymmetric and having undergone no hydrophilic treatment; and a reaction part containing a reagent that reacts with a component to be tested in a sample liquid whose movement has been promoted by said membrane;

wherein said membrane comprises, thicknesswise, a first layer having smaller pores, and a second layer having larger pores, said first layer being held in contact with said reaction part;

and said membrane is laminated on said reaction part.

2. The biosensor according to claim 1, wherein said membrane is provided in the vicinity of said inlet port.

3. The biosensor according to claim 1, wherein said membrane has a plurality of pores each of which is no less than 0.25 μm but no more than 45 μm in diameter.

4. The biosensor according to claim 1, wherein said reaction part and said membrane are formed to extend to said inlet port.

5. The biosensor according to claim 1, wherein the pores of said first layer have a pore diameter of no less than 0.25 μm but no more than 0.45 μm, and the pores of said second layer have a pore diameter of no less than 25 μm but no more tan 45 μm.

6. The biosensor according to claim 1, wherein said capillary has an opening serving as an air escape hole.

7. The biosensor according to claim 1, wherein said capillary has a transparent part or semitransparent part for internally observing said capillary.

8. The biosensor according to claim 7, wherein said membrane is white.

9. The biosensor according to claim 1, further comprising an elongate working electrode and an elongate counter electrode provided on an insulating base, wherein said capillary is formed to intersect said working electrode and said counter electrode on said insulating base.

10. The biosensor according to claim 9, wherein said counter electrode is generally parallel to said working electrode.

11. The biosensor according to claim 9, wherein said capillary comprises a pair of upright walls on said base, and a cover bridging the pair of walls.

12. The biosensor according to claim 1, wherein said membrane draws a sample liquid in a direction of substantially constant pore size in a longitudinal direction of said channel.

13. A method for manufacturing a biosensor which comprises a capillary having a channel with an inlet port for taking in a sample liquid, a membrane for promoting movement of said sample liquid through said channel, and a reaction part containing a reagent that reacts with a component to be tested in said sample liquid whose movement has been promoted by said membrane; the method comprising the steps of:

forming a working electrode and a counter electrode in an elongate configuration on an insulating base;

forming an elongate reaction part intersecting said working electrode and said counter electrode;

laminating an elongate membrane on said reaction part, said membrane being asymmetric and having undergone no hydrophilic treatment;

providing a pair of walls along longitudinal edges on both sides of said reaction part and said membrane; and forming a capillary by forming a cover bridging said pair of walls;

wherein said membrane comprises, thicknesswise, a first layer having smaller pores, and a second layer having larger pores, said first layer being held in contact with said reaction part.

14. The biosensor manufacturing method according to claim 13, wherein said pair of walls is formed by applying a hot melt adhesive.

15. The biosensor manufacturing method according to claim 13, wherein said pair of walls is formed by sticking double-sided tape onto said insulating base.

16. A biosensor for testing a sample liquid, comprising:

a capillary having a channel with an inlet port for taking in a sample liquid;

a membrane for promoting movement of said sample liquid through said channel, said membrane being asymmetric and arranged not to cause hemolysis that lowers measurement accuracy in testing the sample liquid; and a reaction part containing a reagent that reacts with a component to be tested in said sample liquid whose movement has been promoted by said membrane;

wherein said membrane comprises, thicknesswise, a first layer having smaller pores, and a second layer having larger pores, said first layer being held in contact with said reaction part;

and said membrane is laminated on said reaction part.

* * * * *